(12) United States Patent
Kimura et al.

(10) Patent No.: US 7,046,354 B2
(45) Date of Patent: May 16, 2006

(54) SURFACE FOREIGN MATTER INSPECTING DEVICE

(75) Inventors: Syunsuke Kimura, Nishinomiya (JP); Yoshiharu Yamamoto, Toyonaka (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 105 days.

(21) Appl. No.: 10/482,544

(22) PCT Filed: Feb. 24, 2003

(86) PCT No.: PCT/JP03/01961

§ 371 (c)(1),
(2), (4) Date: Dec. 30, 2003

(87) PCT Pub. No.: WO03/073085

PCT Pub. Date: Sep. 4, 2003

(65) Prior Publication Data

US 2004/0169849 A1    Sep. 2, 2004

(30) Foreign Application Priority Data

Feb. 26, 2002    (JP) .............................. 2002-049918

(51) Int. Cl.
*G01N 21/00* (2006.01)

(52) U.S. Cl. ................................. 356/237.2; 356/237.5
(58) Field of Classification Search .. 356/237.1–237.6, 356/239.1, 239.3, 239.7, 394; 250/559.29, 250/559.31
See application file for complete search history.

(56) References Cited

U.S. PATENT DOCUMENTS

| 4,601,576 A | * | 7/1986 | Galbraith .................. 356/237.3 |
| 4,615,620 A | | 10/1986 | Noguchi et al. |
| 4,632,546 A | * | 12/1986 | Sick et al. ................ 356/237.5 |
| 6,201,601 B1 | | 3/2001 | Vaez-Iravani et al. |
| 6,614,519 B1 | * | 9/2003 | Latta et al. ............... 356/237.2 |
| 6,731,384 B1 | * | 5/2004 | Ohshima et al. .......... 356/237.2 |
| 6,774,987 B1 | * | 8/2004 | Komatsu et al. ............... 356/73 |

FOREIGN PATENT DOCUMENTS

| JP | 54-128682 | 10/1979 |
| JP | 60-136324 | 7/1985 |
| JP | 64-4045 | 1/1989 |
| JP | 2-223845 | 9/1990 |

* cited by examiner

*Primary Examiner*—Michael P. Stafira
(74) *Attorney, Agent, or Firm*—Hamre, Schuamnn, Mueller & Larson, P.C.

(57) ABSTRACT

A surface foreign matter inspection device is provided with which the NA can be enlarged with a simple configuration, and a shortening of the time required for foreign matter inspection as well as a high detection sensitivity can be achieved. The device is provided with an optical detection means 6 that irradiates light from an radiation optical system onto the surface of an object under inspection on a stage, reflects light scattered by foreign matter on the object under inspection and turns the reflected light into parallel light, condenses the parallel light with a condensing lens, and detects the condensed light, as well as an information processing device 100 for processing an electrical signal from the optical detection means 6 and position information regarding the foreign matter on the object under inspection 4.

13 Claims, 10 Drawing Sheets

SURFACE FOREIGN MATTER INSPECTING DEVICE

TECHNICAL FIELD

The present invention relates to surface foreign matter inspection devices that detect the state of foreign matter adhering to the surface of a semiconductor substrate.

BACKGROUND ART

Reductions of manufacturing yield in the manufacturing process of semiconductor devices have a direct effect in increasing the product's costs, so that the improvement of manufacturing yield has become an important challenge. One of the main factors leading to a decrease in manufacturing yield is the adherence of foreign matter to the semiconductor substrate, so that there is a strong demand for a technology for detecting the state of adherence of foreign matter efficiently and with high sensitivity.

Conventionally, it is well known to use optical means as a technology for detecting foreign matter on a semiconductor substrate. FIG. 9 is a schematic diagram showing a configuration example of a conventional surface foreign matter inspection device using optical means. In FIG. 9, the conventional surface foreign matter inspection device includes an optical system (radiation optical system (ROS) 5, detection optical system 12), and a control processing system (stage 4a, optical detection means (PDM) 6, information processing device 100). Ordinarily, a laser is used for the radiation optical system 5. The detection optical system 12 is composed of condensing lenses 2 and an optical filter 7a, and focuses light scattered by foreign matter on the semiconductor substrate.

Using this device, foreign matter on a silicon wafer 4 can be inspected as follows. Laser light is irradiated from the radiation optical system 5 onto the silicon wafer 4, which is placed on the stage 4a. Then, when foreign matter is present at the location onto which the laser light is irradiated, the reflected light that is scattered by this foreign matter is captured in the detection optical system 12, condensed by the detection optical system 12, and the condensed light is converted into an electrical signal by the optical detection means 6. By processing this electrical signal with the information processing device 100, and by also processing information about the position of the foreign matter on the silicon wafer 4 in the information processing device 100, foreign matter on the silicon wafer 4 can be inspected. In the surface foreign matter inspection device using such optical means, in order to detect foreign matter of even tinier size with high sensitivity, the intensity of the irradiated light is enhanced, the sensitivity of the optical detector 6 is enhanced, or the focusing ability of the optical system is improved.

If the detection optical system 12 composed of ordinary optical elements as shown in FIG. 9 is used, then increasing the NA (numerical aperture) of the optical system in order to improve its focusing ability leads to the problem that the size of the detection optical system 12 becomes large, resulting in interference with light irradiated from the radiation optical system 5.

On the other hand, when an optical element of an optically reflective system, for example a parabolic mirror, is used for the detection optical system 12, then reflected light can be captured over a broad scanning range on the object under inspection while avoiding interference with the irradiated light due to the relatively small size of the detection optical system 12.

However, with such a detection optical system, the region over which the reflected light can be captured without aberrations is restricted to one point on the optical axis of the parabolic mirror, so that the object point range on the object under inspection over which the detection optical system can capture the reflected light, becomes narrow, and as a result, the scanning range of the radiation optical system on the object under inspection becomes small. Thus, the amount of scanning by the radiation optical system over the object under inspection becomes very large, and a long time is needed to inspect for foreign matter.

It is thus an object of the present invention to solve these problems of the prior art and to provide a surface foreign matter inspection device, with which the NA of the optical system can be enlarged with a simple configuration, and the shortening of the time required for foreign matter inspection as well as a high detection sensitivity can be achieved.

DISCLOSURE OF THE INVENTION

In order to attain this object, a surface foreign matter inspection device according to the present invention uses an optical means to inspect foreign matter on an object under inspection, and includes a stage on which the object under inspection is placed and moved; a light irradiation means for irradiating light onto a surface of the object under inspection; a focusing means including a first cylindrical mirror that reflects light scattered by foreign matter on the object under inspection and turns that light into parallel light, and a condensing lens for condensing the parallel light or a second cylindrical mirror whose optical axis substantially coincides with the optical axis of the first cylindrical mirror; an optical detection means for receiving the condensed light from the focusing means and converting it into an electrical signal; and an information processing device for processing the electrical signal that is output from the optical detection means and position information regarding the foreign matter on the object under inspection.

With this configuration, the NA of the optical system can be enlarged with a simple configuration, the object point range on the object under inspection over which the detection optical system can capture the reflected light is broadened. The scanning range of the radiation optical system on the object under inspection is enlarged. The distance over which the irradiated light is scanned is shortened, and also the time required for foreign matter inspection becomes shorter. Moreover, the amount of light scattered by the foreign matter that can be captured becomes large, so that the detection sensitivity of the surface foreign matter inspection device can be increased.

BEST MODE FOR CARRYING OUT THE INVENTION

The following is a detailed explanation of preferred embodiments of the present invention, with reference to the accompanying drawings.

Embodiment 1

Figure 1:
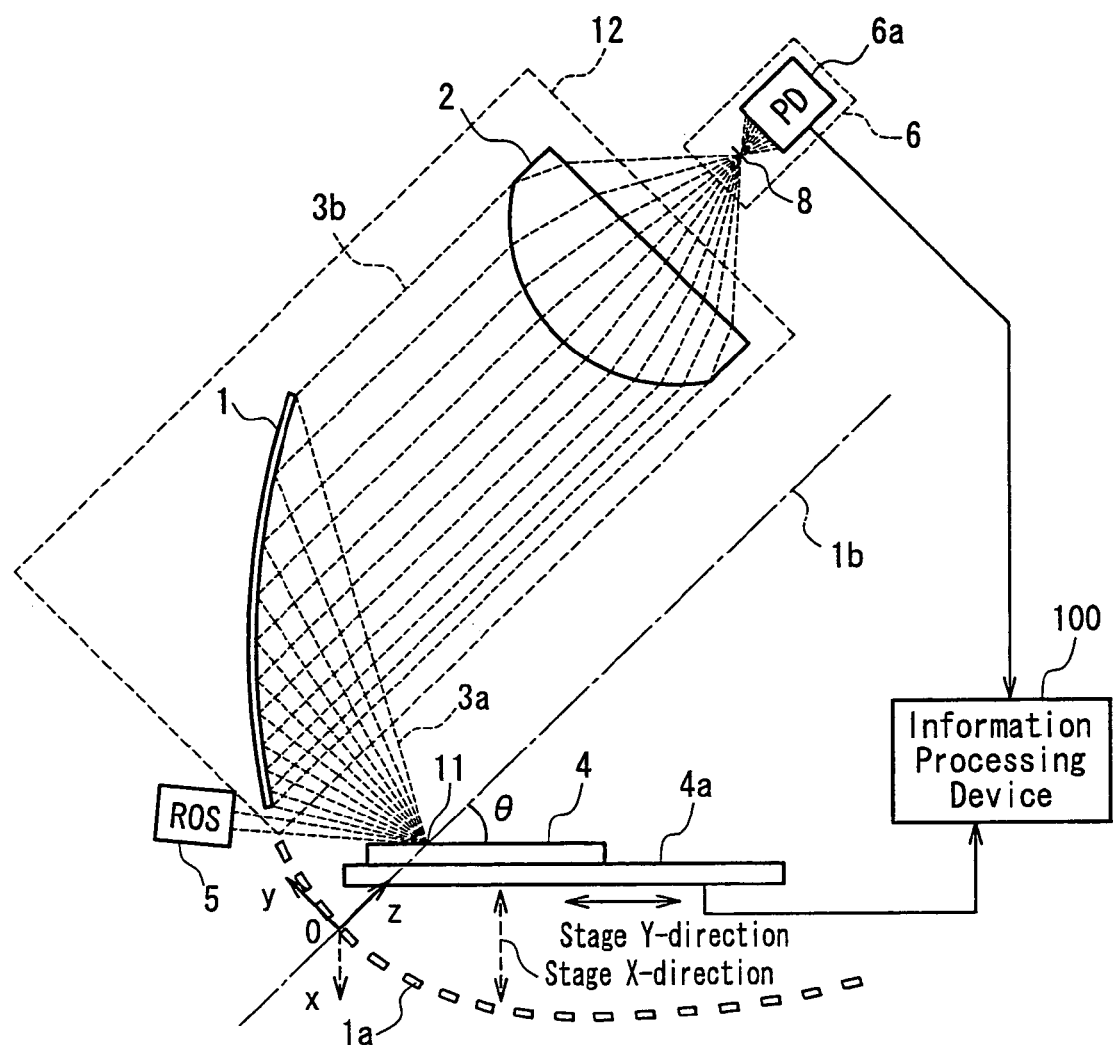
FIG. 1 is a schematic diagram showing a configuration of a surface foreign matter inspection device according to Embodiment 1 of the present invention.
Figure 9:
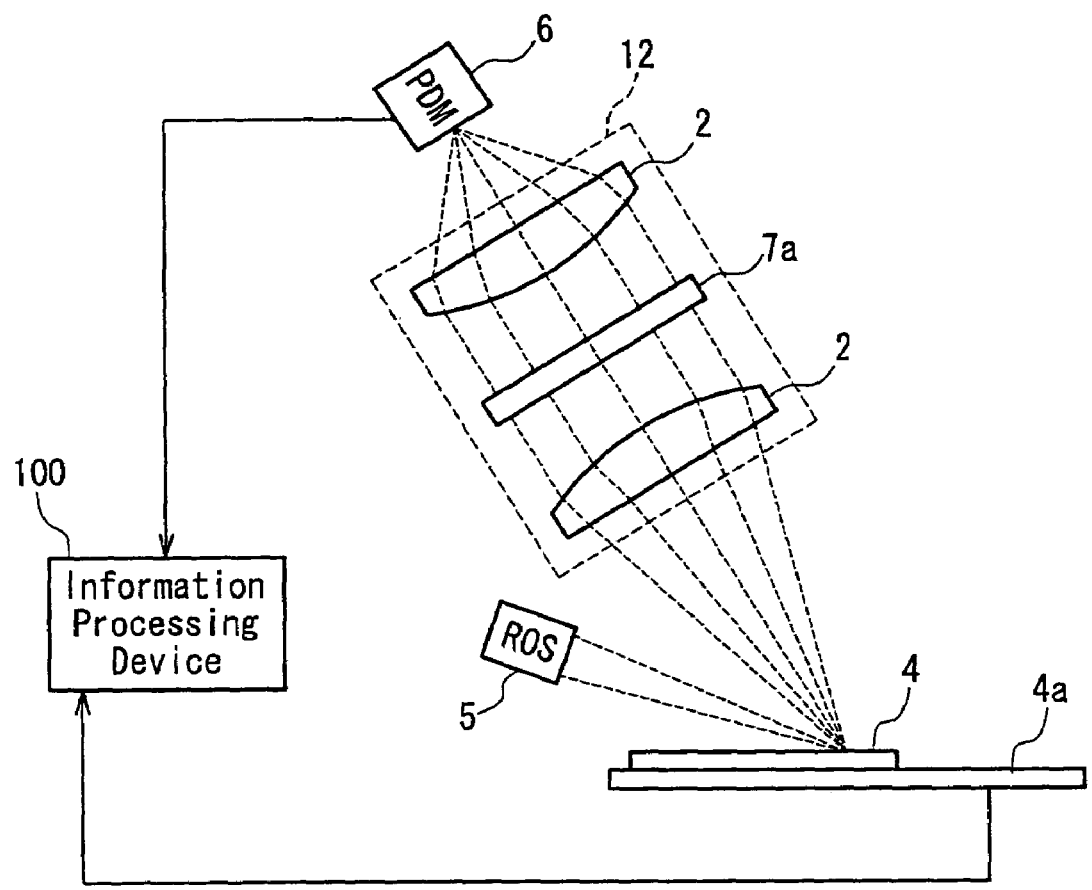
FIG. 9 is a schematic diagram showing a configuration of a conventional surface foreign matter inspection device.

FIG. 1 is a schematic diagram showing a configuration of a surface foreign matter inspection device according to Embodiment 1 of the present invention. The configuration of this device is similar to that of the conventional surface foreign matter inspection device explained with reference to FIG. 9, except that the detection optical system 12 (focusing means) is configured by a cylindrical mirror 1 (first cylindrical mirror), which has a columnar surface or a substantially columnar surface, and a condensing lens 2 (condensing means), which has a rotation-symmetric shape. Consequently, portions having the same configuration and function as in the conventional example are given the same numerals, and their further explanation has been omitted.

In FIG. 1, numeral 1a denotes an extension surface (virtual surface) of the cylindrical mirror 1, numeral 1b denotes the optical axis of the cylindrical mirror 1, and numeral 11 denotes the irradiation position of the radiation optical system 5 (optical radiation means). A slit 8 at the focus position of the condensed light beam, and a photo-detector (PD) 6a converting the intensity of the condensed light into an electrical signal are disposed inside the optical detection means 6. It should be noted that also in the following embodiments, the detection optical system 12 is configured by a mirror and a lens.

The coordinate system in FIG. 1 is as follows. That is, in the detection optical system 12, the intersection (point O in the figure) of the optical axis 1b of the cylindrical mirror 1 and the extension surface 1a of the cylindrical mirror 1 is taken as the point of origin, the direction of the optical axis 1b is taken as the z-axis, the direction perpendicular to the optical axis 1b and parallel to the direction of the lens effect of the cylindrical mirror 1 is taken as the y-axis, and the direction perpendicular to the z-axis and the y-axis is taken as the x-axis, as shown in the figure. As for the stage 4a, the direction on the stage 4a that is parallel to the projection line of the optical axis 1b onto the stage 4a is taken as the Y-direction, and the direction on the stage 4a that is perpendicular to the Y-direction is taken as the X-direction.

Using this device, foreign matter on the silicon wafer 4, which is to be inspected, can be inspected in the following manner. While scanning the stage 4a in accordance with a predetermined pattern in the X-Y direction, light is irradiated from the radiation optical system 5 onto the wafer 4 placed on the stage 4a. At this time, when there is foreign matter at the irradiation position of the irradiated light, then the irradiated light is scattered by the foreign matter, thereby generating scattered light 3a. Here, in order to capture the scattered light 3a without causing aberration, it is preferable that the light is irradiated such that the irradiation position 11 is on the optical axis 1b of the cylindrical mirror 1.

The scattered light 3a is captured by the detection optical system 12 and reflected by the cylindrical mirror 1. The parallel light 3b that advances in a direction parallel to the optical axis 1b is condensed with a condensing lens 2 and introduced into the optical detection system 6, and after the condensed light has passed through the slit 8 at the focus position, it is received by the photo-detector 6a, which converts the intensity of the condensed light beam into an electrical signal.

This electrical signal is processed by an information processing device 100, and the size and shape of the foreign matter are identified. At the same time, also the position information of the foreign matter on the silicon wafer 4 is captured from the stage 4a, and processed by the information processing device 100.

By using the cylindrical mirror 1, the working distance of the radiation optical system 5, that is, the object point range on the object under inspection over which the detection optical system can capture the reflected light is broadened, and the scattered light 3a that is scattered by the foreign matter can be captured selectively and in a large amount, so that the focusing ability of the detection optical system 12 is improved considerably. Moreover, the space inside the device that is taken up by the detection optical system 12 does not become any larger, so that there is also no interference with the irradiated light of the radiation optical system 5. It should be noted that it is preferable that the cylindrical mirror 1 is disposed such that the angle θ (°) defined by its optical axis 1b and the surface of the silicon waver 4 becomes 0°<θ<60°. This is because, if θ is 60° or larger, then the space inside the device that is taken up by the detection optical system 12 becomes large, which results in interference between the scattered light 3a of the detection optical system 12 and the irradiated light of the radiation optical system 5.

In this embodiment, the detection optical system 12 can be configured by disposing optical elements having the following characteristics inside the device:

D1 (mm): distance between the irradiation position 11 and the cylindrical mirror 1 of the detection optical system in the direction of the optical axis 1b;

R1$x$ (mm): curvature radius of the cross-sectional shape of the cylindrical mirror 1 in the zx-plane;

R1$y$ (mm): curvature radius of the cross-sectional shape of the cylindrical mirror 1 in the yz-plane;

D11 (mm): distance between the cylindrical mirror 1 and the condensing lens 2 in the direction of the optical axis 1b;

D2 (mm): lens thickness of the condensing lens 2;

R21 (mm): curvature radius of the cross-sectional shape of the condensing lens 2 in the yz-plane on the light incident surface side;

R22 (mm): curvature radius of the cross-sectional shape of the condensing lens 2 in the yz-plane on the light output surface side;

Nd2 (−): refractive index of the condensing lens 2 on the optical axis;

vd2 (–): Abbe number of the condensing lens 2 on the optical axis;

D12 (mm): distance between the condensing lens 2 and the photo-detector 6 of the detection optical system in the direction of the optical axis 1b; and D1=40 mm, R1x=∞, R1y=80 mm, D11=46.83 mm, D2=140 mm, R21=43.8104 mm, R22=–240.8968 mm, Nd2=1.60970, vd2=57.8, D12=38.28 mm.

For the cylindrical mirror 1, it is possible to use a mirror of a parabolic shape whose cross-section in the yz-plane can be expressed by:

$$z=y^2/(2\times r) \quad (1)$$

Here, r=80 mm (=R1y).

Moreover, for the equation expressing the cross-sectional shape in the respective yz-planes of the condensing lens 2 at the light incident surface side and the light output surface side, the following general equation (2) is used:

$$z=(h^2/r)/(1+(1-(1+k)(h/r)^2)^{1/2}+A4\times h^4+A6\times h^6+A8\times h^8+A10\times h^{10} \quad (2)$$

(In Eq. (2), h is the distance from the point of origin O in y-axis direction. z indicates the distance between the y-axis and the cross-sectional shape at the position y=h). The following numerical values are used in the Equation (2) representing the cross-sectional shape at the light incident surface side of the condensing lens 2:

$k=-0.347, r=43.8$ mm$(=R21), A4=-4.05\times 10^{-7}$,
$A6=-1.78\times 10^{-10}, A8=-2.26\times 10^{-14}, A10=-2.81\times 10^{-17}$.

Furthermore, the following numerical values are used in the Equation (2) representing the cross-sectional shape at the light output surface side of the condensing lens 2:

$k=-15.734, r=-240.9$ mm$(=R22), A4=2.06\times 10^{-7}$,
$A6=-3.57\times 10^{-10}, A8=-7.91\times 10^{-14}, A10=-5.68\times 10^{-17}$.

With this configuration, the scanning range of the radiation optical system on the silicon wafer 4 is ±0 mm in the Y-direction and ±5 mm in the X-direction, which is a generous value, taking the X-Y direction on the stage 4a as a reference.

In this embodiment, in order to obtain a small and stable light beam, it is preferable to use laser light as the irradiated light of the radiation optical system 5, and in order to obtain more detailed information about the position of the foreign matter, it is preferable that the spot diameter of the laser light is in the range of 0.003 to 0.03 mm. Furthermore, in order to enable detection of light beams with a very small spot diameter in the optical detection means 6, it is preferable to use a photomultiplier tube (photomultiplier) for the photo-detector 6a. It should be noted that other than laser light, it is also possible to use visible light from a lamp, and in this case, a CCD may be used instead of a photomultiplier tube for the photo-detector 6a.

According to this embodiment, by using a cylindrical mirror for the detection optical system, the NA of the optical system can be enlarged with a simple configuration, and the object point range on the object under inspection over which the detection optical system can capture reflected light can be broadened, the scanning range of the radiation optical system on the object to be inspected can be enlarged, and the distance over which irradiated light is scanned is shortened, so that the time needed for the foreign matter inspection is shortened. Moreover, a large amount of the light scattered by the foreign matter can be captured, and the detection sensitivity of the surface foreign matter inspection device can be increased.

Embodiment 2

Figure 2:
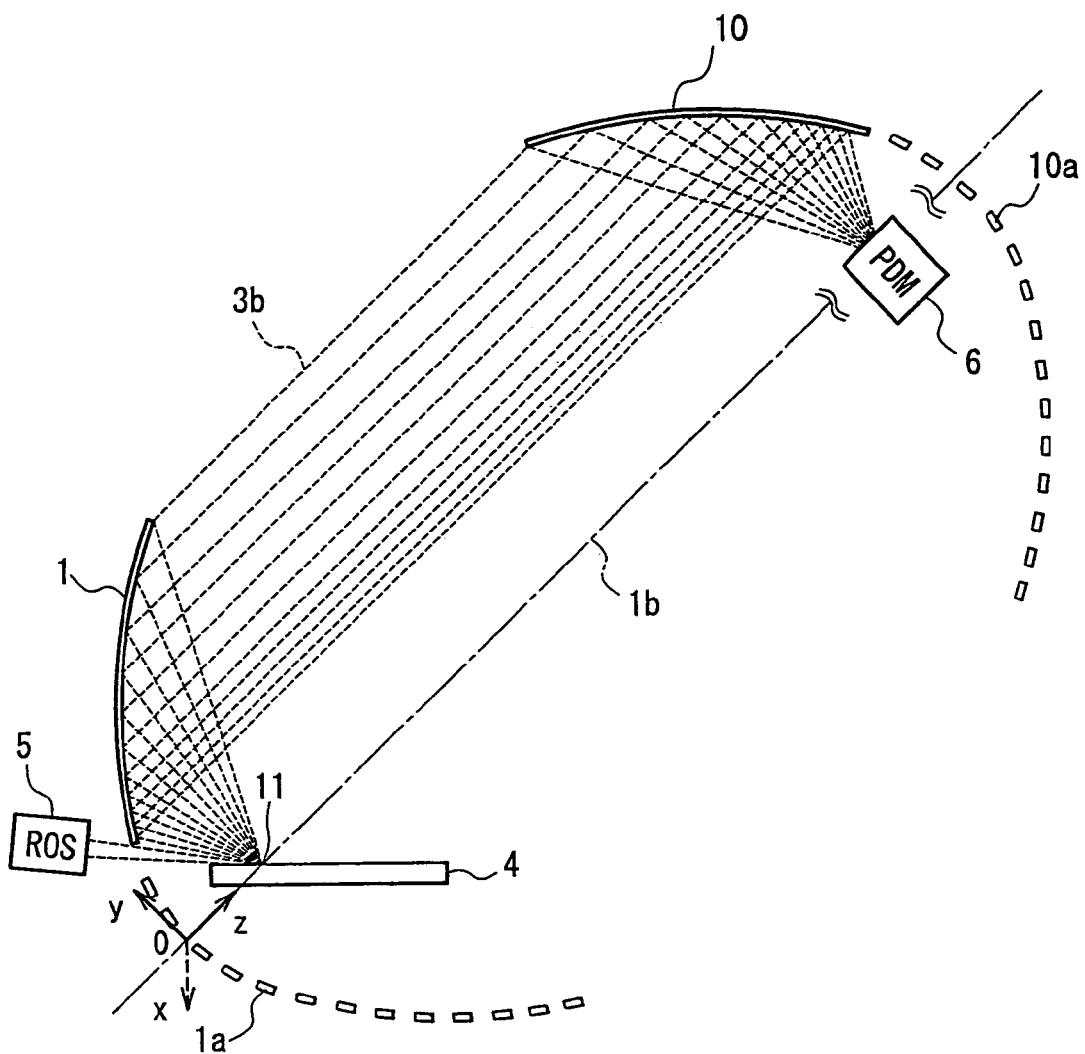
FIG. 2 is a schematic diagram showing a configuration of a surface foreign matter inspection device according to Embodiment 2 of the present invention.

FIG. 2 is a schematic diagram showing a configuration of a surface foreign matter inspection device according to an embodiment of the present invention. The configuration of this device is similar to that of the device in Embodiment 1 (FIG. 1), except that in the detection optical system 12 of Embodiment 1, a cylindrical mirror 10 (second cylindrical mirror serving as light condensing means) whose optical axis substantially coincides with that of the cylindrical mirror 1 (first cylindrical mirror) is used instead of the condensing lens 2. In FIG. 2, numeral 10a denotes the extension surface (virtual surface) of the cylindrical mirror 10. Other portions corresponding to FIG. 1 have been given the same numerals, and their further explanation has been omitted. The coordinate system is the same as in FIG. 1.

Using this embodiment, foreign matter on the silicon wafer 4 can be inspected as follows. As in Embodiment 1, irradiation light is irradiated onto the foreign matter to generate scattered light 3a, the scattered light 3a is captured by the detection optical system, reflected by the cylindrical mirror 1 and turned into parallel light 3b, which is then condensed by the cylindrical mirror 10, and the condensed light is introduced into the optical detection means 6. After that, the same processing as in Embodiment 1 is carried out.

In this embodiment, the detection optical system 12 can be configured, for example, by using for example cylindrical mirrors with the same characteristics as the cylindrical mirror 1 of Embodiment 1 for the cylindrical mirror 1 and the cylindrical mirror 10, and by disposing them to set the distance D100 between the cylindrical mirror 1 and the cylindrical mirror 10 of the detection optical system in the direction of the optical axis 1b, to D100=300 mm.

With this configuration, the scanning range of the radiation optical system on the silicon wafer 4 is ±0 mm in the Y-direction and ±5 mm in the X-direction, which is a generous value, taking the X-Y direction on the stage 4a as a reference.

It should be noted that in this embodiment, the focused light beam that is introduced into the optical detection means 6 has a certain width in the Z-direction, so that it is preferable that the shape of the window portion of the optical detection means 6 has an oblong, substantially rectangular shape.

According to the present embodiment, similar effects as those of Embodiment 1 are attained, and moreover by using a cylindrical mirror 10 instead of the condensing lens 2, aberrations due to the condensing lens 2 are reduced, and the focusing efficiency of the scattered light 3a is improved and the detection sensitivity of the surface foreign matter inspection device is increased in comparison with Embodiment 1.

Embodiment 3

Figure 3:
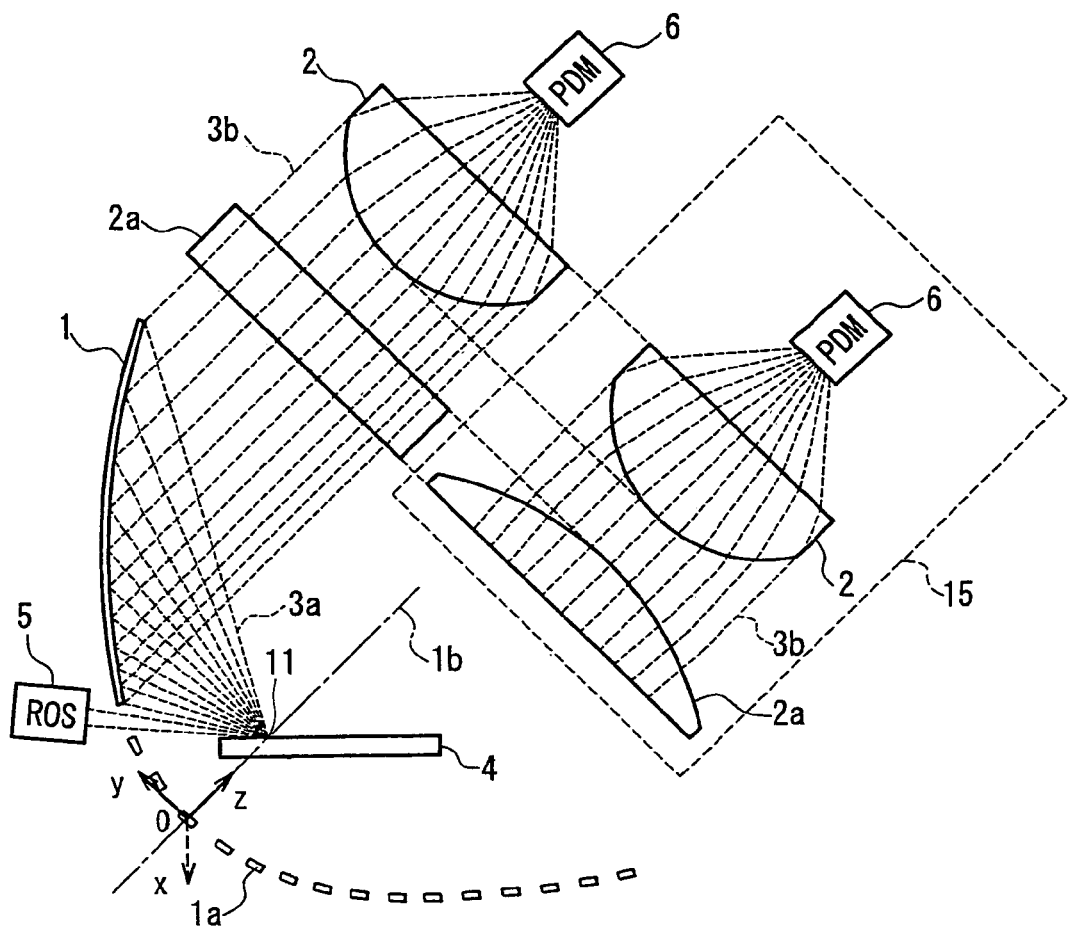
FIG. 3 is a schematic diagram showing a configuration of a surface foreign matter inspection device according to Embodiment 3 of the present invention.

FIG. 3 is a schematic diagram showing a configuration of a surface foreign matter inspection device according to Embodiment 3 of the present invention. The configuration of this device is similar to that of the device in Embodiment 1 (FIG. 1), except that in the detection optical system 12 of Embodiment 1, a cylindrical lens 2a having a lens effect in the x-axis direction is disposed between the cylindrical mirror 1 and the condensing lens 2. Other portions corresponding to FIG. 1 have been given the same numerals, and their further explanation has been omitted. Also the coordinate system is the same as in FIG. 1. It should be noted that in FIG. 3, numeral 15 denotes a cross-sectional view taken along the zx-plane of the cylindrical lens 2a and the condensing lens 2 (in the following embodiments, the corresponding portions of the referenced drawings are the same).

Using this device, foreign matter on the silicon wafer 4 can be inspected as follows. As in Embodiment 1, irradiation light is irradiated onto the foreign matter to generate scattered light 3a, the scattered light 3a is captured by the detection optical system 12, reflected by the cylindrical mirror 1 and turned into parallel light 3b. Then, the parallel light 3b passes through the cylindrical lens 2a, and after light that has been dispersed in the x-axis direction by the reflection with the cylindrical mirror 1 is corrected in a direction parallel to the optical axis 1b with the cylindrical lens 2a, it is condensed with the condensing lens 2 and the condensed light is introduced into the optical detection means 6. After that, the same processing as in Embodiment 1 is performed.

The cylindrical lens 2a is preferably disposed such that the direction of the lens effect of the cylindrical lens 2a is substantially perpendicular to the direction of the lens effect of the cylindrical mirror 1, because this allows the scattered light 3a from the foreign matter on the silicon wafer 4 to be focused efficiently.

In this embodiment, the detection optical system 12 can be configured, for example, by disposing for a cylindrical mirror 1 and a condensing lens 2, optical elements having the same characteristics as those in Embodiment 1 inside the device, and furthermore disposing a cylindrical lens 2a with the following characteristics and in the following manner:

D20 (mm): distance between the cylindrical mirror 1 and the cylindrical lens 2 of the detection optical system in the direction of the optical axis 1b;

R23a (mm): curvature radius of the cross-sectional shape of the cylindrical lens 2a on the light incident surface side in the yz-plane;

R23b (mm): curvature radius of the cross-sectional shape of the cylindrical lens 2a on the light incident surface side in the zx-plane;

R24a (mm): curvature radius of the cross-sectional shape of the cylindrical lens 2a on the light output surface side in the yz-plane;

R24b (mm): curvature radius of the cross-sectional shape of the cylindrical lens 2a on the light output surface side in the zx-plane;

D21 (mm): lens thickness of the cylindrical lens 2a;

Nd3 (−): refractive index of the cylindrical lens 2a on the optical axis;

vd3 (−): Abbe number of the cylindrical lens 2a on the optical axis;

D22 (mm): distance between the cylindrical lens 2a and the condensing lens 2 of the detection optical system in the direction of the optical axis 1b; and D20=140 mm, R23a=∞, R23b=∞, R24a=−159.8 mm, R24b=∞, D21=28.5 mm, Nd3=1.80518, vd3=25.5, D22=20 mm.

Moreover, for the cylindrical lens 2a, a non-circular arc-shaped lens is used whose cross-sectional shape in the zx-plane is obtained by inserting the following values in the above-noted general formula (2):

$k=-0.765, r=-159.8$ mm $(=R24a), A4=0, A6=0,$
$A8=0, A10=0$

With this configuration, the scanning range of the radiation optical system on the silicon wafer 4 is ±0 mm in the Y-direction and ±5 mm in the X-direction, which is a generous value, taking the X-Y direction on the stage 4a as a reference.

With the present embodiment, similar effects as with Embodiment 1 are attained, and moreover aberrations due to light rays of the scattered light reflected by the cylindrical mirror 1 that are dispersed in a direction perpendicular to the direction of the lens effect of the cylindrical mirror 1 are corrected effectively by the cylindrical lens 2, and the focusing efficiency of the scattered light 3a is improved and the detection sensitivity of the surface foreign matter inspection device is increased in comparison with Embodiment 1.

Embodiment 4

Figure 4:
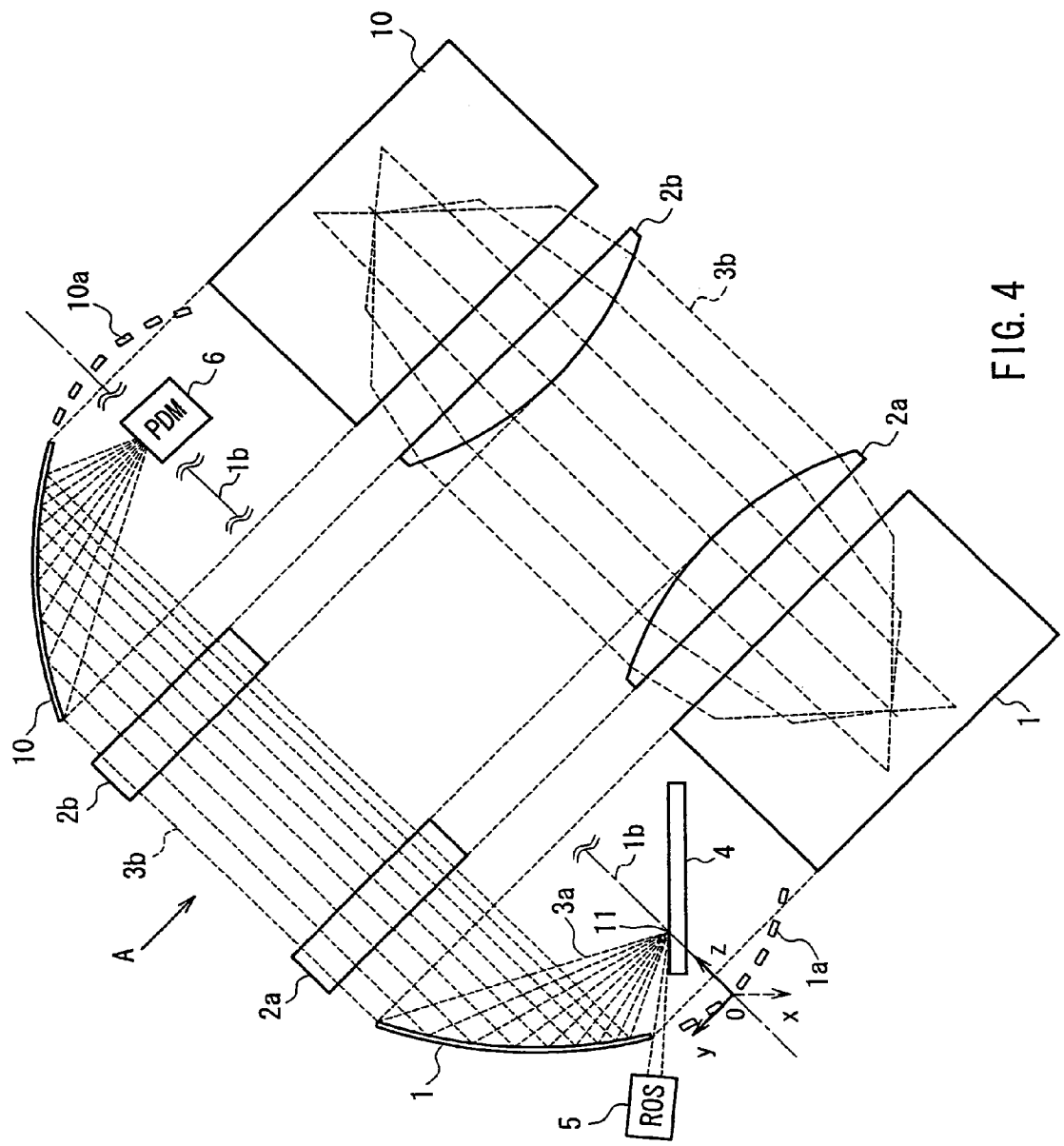
FIG. 4 is a schematic diagram showing a configuration of a surface foreign matter inspection device according to Embodiment 4 of the present invention.

FIG. 4 is a schematic diagram showing a configuration of a surface foreign matter inspection device according to Embodiment 4 of the present invention. The configuration of this device is similar to that of the device in Embodiment 2 (FIG. 2), except that in the detection optical system 12 of Embodiment 2, a pair of cylindrical lenses 2a and 2b whose columnar surfaces are opposed to each other and that have a lens effect with respect to substantially the same direction are disposed between the cylindrical mirror 1 (first cylindrical mirror) and a cylindrical mirror 10 (second cylindrical mirror). It should be noted that FIG. 4 also shows the pair of cylindrical lenses 2a and 2b as well as the cylindrical mirrors 1 and 10 as viewed from a direction A. Other portions corresponding to FIG. 2 have been given the same numerals, and their further explanation has been omitted. Also the coordinate system is the same as in FIG. 2.

Using this device, foreign matter on the silicon wafer 4 can be inspected as follows. As in Embodiment 1, irradiation light is irradiated onto the foreign matter to generate scattered light 3a, the scattered light 3a is captured by the detection optical system 12, reflected by the cylindrical mirror 1 and turned into parallel light 3b. Then, the parallel light 3b passes through the cylindrical lenses 2a and 2b, and after light that has been dispersed in the x-axis direction by the reflection with the cylindrical mirror 1 is corrected in a direction parallel to the optical axis 1b by the cylindrical lenses 2a and 2b, it is condensed with the cylindrical mirror 10 and the condensed light is introduced into the optical detection means 6. After that, the same processing as in Embodiment 1 is performed.

As in the present embodiment, the cylindrical lenses 2a and 2b are preferably disposed such that the direction of the lens effect of the cylindrical lenses 2a and 2b is substantially perpendicular to the direction of the lens effect of the cylindrical mirror 1, because this allows the scattered light 3a from the foreign matter on the silicon wafer 4 to be focused with high efficiency.

In this embodiment, the detection optical system 12 can be configured, for example, by disposing for the cylindrical mirror 1 and the cylindrical mirror 10 optical elements having the same characteristics as those in Embodiment 2 inside the device. Further, for the cylindrical lenses 2a and 2b, lenses with the same characteristics as the cylindrical lens 2a in Embodiment 3 can be used. Furthermore, the distance D25 between the cylindrical lenses 2a and 2b in the direction of the optical axis 1b of the detection optical system is set to D25=117.28 mm. It should be noted that in this embodiment, it is also possible to condense the parallel light 3b using a condensing lens 2 having an axially symmetric shape as shown in Embodiment 1 instead of the cylindrical mirror 10.

With this configuration, the scanning range of the radiation optical system on the silicon wafer 4 is ±0 mm in the Y-direction and ±5 mm in the X-direction, which is a generous value, taking the X-Y direction on the stage 4a as a reference.

It should be noted that in this embodiment, the condensed light beam that is introduced into the optical detection means 6 has a certain width in the z-direction, so that it is preferable that the shape of the window portion of the optical detection means 6 has an oblong, substantially rectangular shape.

According to the present embodiment, similar effects as for Embodiment 2 are attained, and moreover aberrations due to light rays of the scattered light reflected by the cylindrical mirror 1 that are dispersed in a direction perpendicular to the direction of the lens effect of the cylindrical mirror 1 are corrected effectively by the pair of cylindrical lenses 2a and 2b, whose columnar surfaces are opposed to each other in the detection optical system and that have a lens effect with respect to substantially the same direction, and the focusing efficiency of the scattered light 3a is improved and the detection sensitivity of the surface foreign matter inspection device is increased in comparison with Embodiment 1.

Embodiment 5

Figure 5:
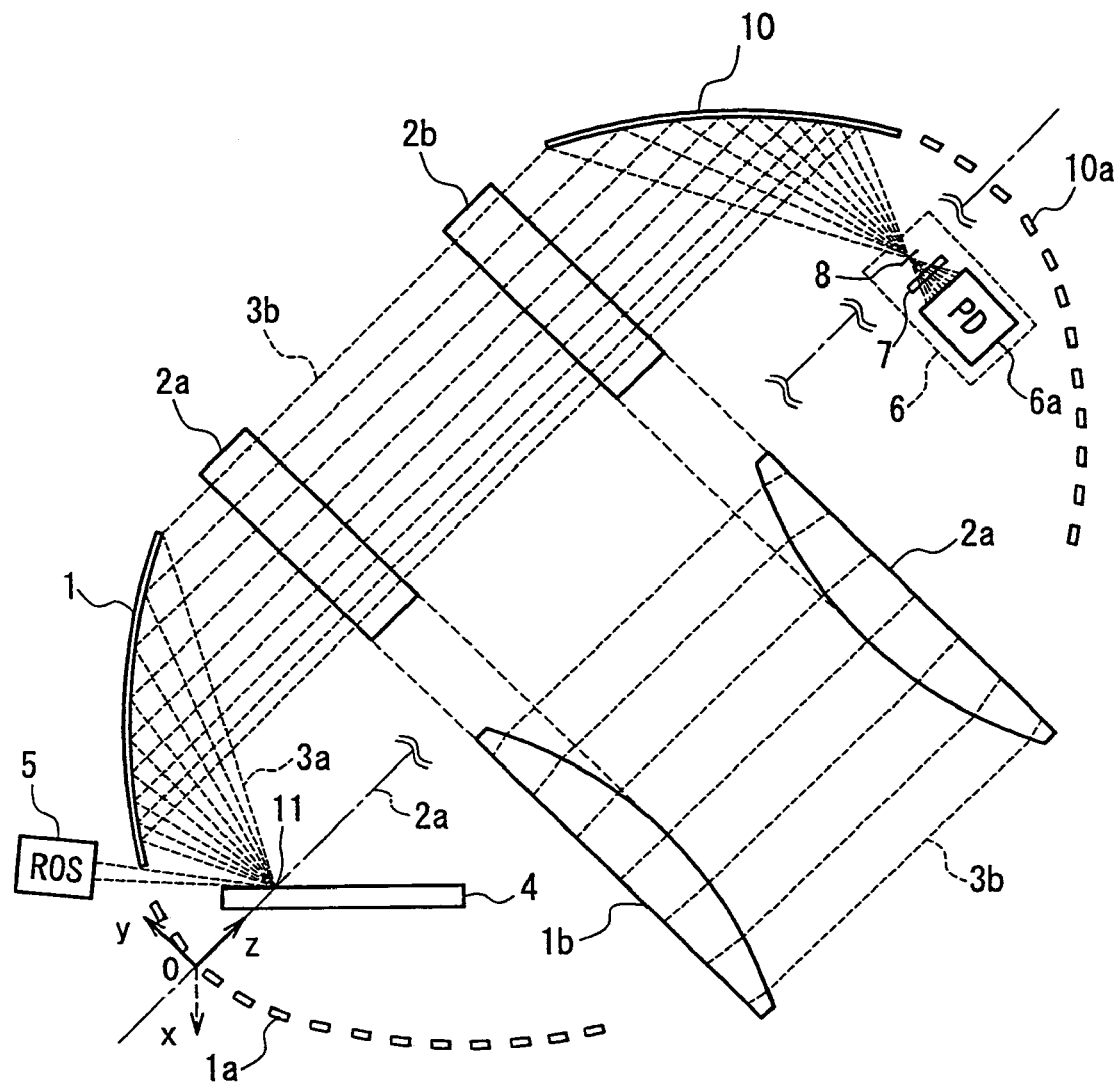
FIG. 5 is a schematic diagram showing a configuration of a surface foreign matter inspection device according to Embodiment 5 of the present invention.

FIG. 5 is a schematic diagram showing a configuration of a surface foreign matter inspection device according to Embodiment 5 of the present invention. The configuration of this device is similar to that of the device in Embodiment 4 (FIG. 4), except that in the optical detection means 6 of Embodiment 4, a polarization filter 7 is disposed between the slit 8 and the photo-detector 6a.

In FIG. 5, the polarization filter 7 is movable and can be switched between a state in which it is placed on the light path of the condensed light and a state in which it is removed from the light path in the optical detection means 6. Other portions corresponding to FIG. 4 have been given the same numerals, and their further explanation has been omitted. Also the coordinate system is the same as in FIG. 4.

Using this embodiment, foreign matter on the silicon wafer 4 can be inspected as follows. As in Embodiment 1, irradiation light is irradiated onto the foreign matter to generate scattered light 3a, the scattered light 3a is captured by the detection optical system 12, reflected by the cylindrical mirror 1 and turned into parallel light 3b. Then, the parallel light 3b passes through the cylindrical lenses 2a and 2b and after light that has been dispersed in the x-axis direction by the reflection with the cylindrical mirror 1 is corrected in a direction parallel to the optical axis 1b by the cylindrical lenses 2a and 2b it is condensed with the cylindrical mirror 10 and the condensed light is introduced into the optical detection means 6. Then, after the condensed light has passed through the slit 8 at the focus position, it passes further through the polarization filter 7, which turns the condensed light into plane polarized light, and the intensity of this plane polarized light is converted into an electric signal by the photo-detector 6a. After that, the same processing as in Embodiment 1 is performed.

In this embodiment, foreign matter on the silicon wafer 4, and structural unevenness such as wiring or the like, can be discriminated by the polarization filter 7. That is to say, in the case of scattered light from foreign matter, the polarization state of the light is at random, and the amplitude of the electrical signal that is output from the optical detection means 6 changes greatly depending on whether the polarization filter 7 is in place or not. On the other hand, in the case of reflected light from structural unevenness on the silicon wafer 4, the polarization state of the light is maintained, and there is almost no change in the amplitude of the electrical signal that is output from the optical detection means 6, regardless of whether the polarization filter 7 is in place or not. Utilizing this principle, by adjusting the state of the polarization filter 7 by rotation, it can be discriminated whether the detected light is scattered light from foreign matter or reflected light from structural unevenness.

In this way, when disposing the polarization filter 7 in the optical detection means 6, it is preferable that it is disposed between the slit 8 and the photo-detector 6a. Thus, no aberrations occur in the condensed light, and the intensity of the detected light can be increased.

In the present embodiment, the polarization filter 7 and the slit 8 can be configured, for example, by disposing optical elements having the following characteristics:

D26 (mm): thickness of the slit 8;

R25 (mm): curvature radius of the cross-sectional shape of the slit 8 in the yz-plane;

R26a(mm): curvature radius of the cross-sectional shape of the polarization filter 7 on the light incident surface side in the yz-plane;

R26b (mm): curvature radius of the cross-sectional shape of the polarization filter 7 on the light output surface side in the yz-plane;

Nd4 (−): refractive index of the polarization filter 7 on the optical axis;

vd4 (−): Abbe number of the polarization filter 7 on the optical axis;

D27 (mm): thickness of the polarization filter 7;

D28 (mm): distance between the slit 8 and the polarization filter 7 in the direction of the optical axis 1b of the detection optical system; and D26=10 mm, R25=∞, R26a=∞, R26b=∞, Nd4=1.51680, vd4=64.2, D27=2 mm, D28=8 mm.

With this configuration, the scanning range of the radiation optical system on the silicon wafer 4 is ±0 mm in the Y-direction and ±5 mm in the X-direction, which is a generous value, taking the X-Y direction on the stage 4a as a reference.

According to the present embodiment, similar effects as with Embodiment 4 are attained, and moreover by suitably disposing a polarization filter 7 inside the optical detection means 6, it is possible to focus only the scattered light from the foreign matter selectively and efficiently, thus increasing the detection sensitivity of the surface foreign matter inspection device in comparison with Embodiment 4.

Embodiment 6

Figure 6:
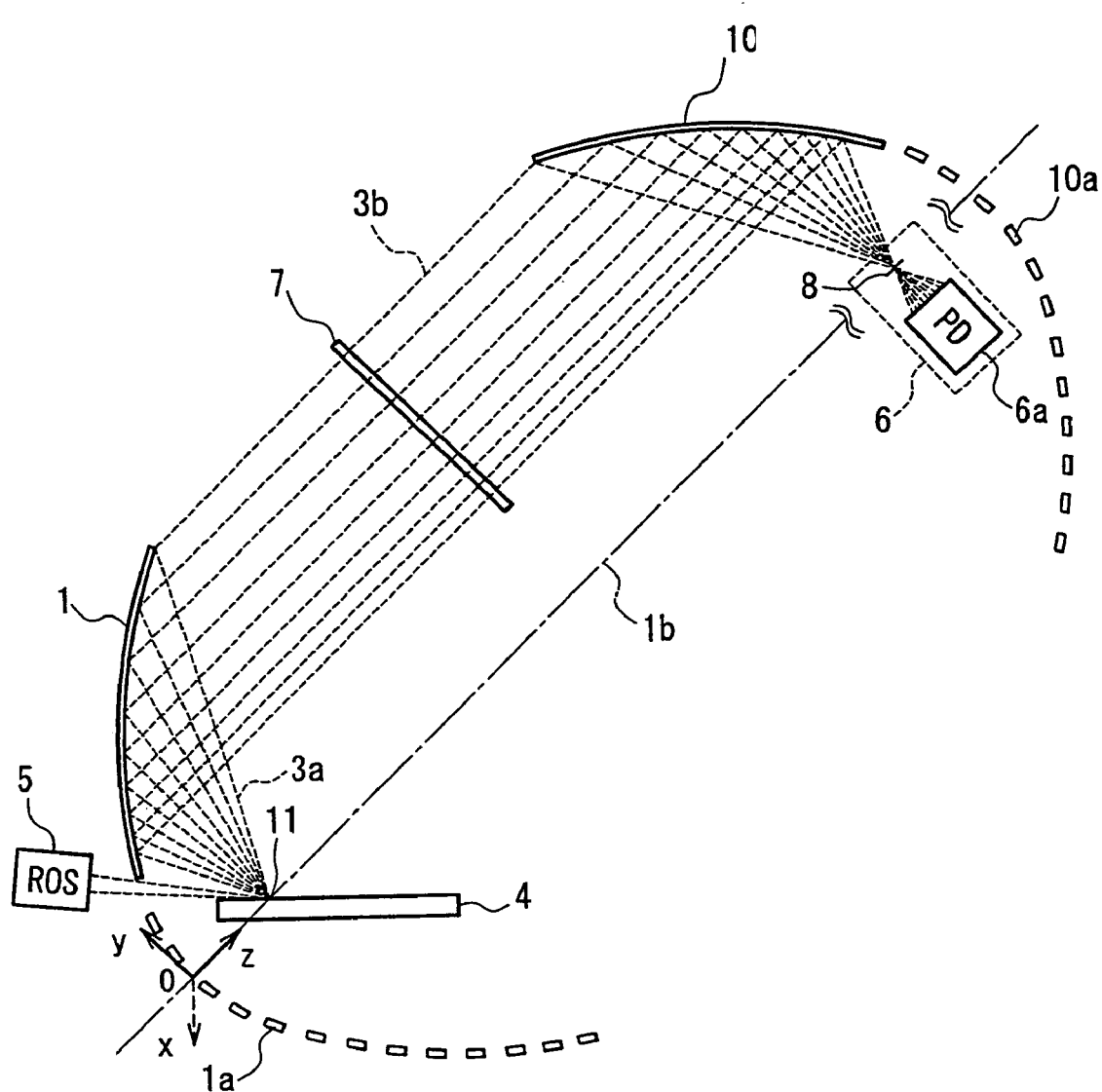
FIG. 6 is a schematic diagram showing a configuration of a surface foreign matter inspection device according to Embodiment 6 of the present invention.

FIG. 6 is a schematic diagram showing a configuration of a surface foreign matter inspection device according to Embodiment 6 of the present invention. The configuration of this device is similar to that of the device in Embodiment 2 (FIG. 2), except that in the optical detection means 12 of Embodiment 2, a polarization filter 7 is disposed between the cylindrical mirror 1 (first cylindrical mirror) and the cylindrical mirror 10 (second cylindrical mirror).

In FIG. 6, the polarization filter 7 is movable and can be switched between a state in which it is placed on the light path of the parallel light 3b and a state in which it is left from the light path in the detection optical system 12. Other portions corresponding to FIG. 2 have been given the same numerals, and their further explanation has been omitted. Also the coordinate system is the same as in FIG. 2.

Using this embodiment, foreign matter on the silicon wafer 4 can be inspected as follows. As in Embodiment 1, irradiation light is irradiated onto the foreign matter to generate scattered light 3a, and the scattered light 3a is captured by the detection optical system 12, reflected by the cylindrical mirror 1 and turned into parallel light 3b. Then, the parallel light 3b passes through the polarization filter 7, which turns it into planar polarized light. Then, it is condensed by the cylindrical mirror 10, and introduced into the optical detection means 6. Next, after the condensed light has passed through the slit 8 at the focus position, the intensity of the condensed light is converted into an electric signal by the photo-detector 6a. After that, the same processing as in Embodiment 1 is performed.

In this embodiment, the same effect as with the polarization filter 7 in Embodiment 5 can be attained with the polarization filter 7, and foreign matter on the silicon wafer 4, and structural unevenness such as wiring or the like, can be discriminated. It should be noted that it is preferable that the polarization filter 7 is disposed between the cylindrical mirror 1 and the cylindrical mirror 10 in a region where the scattered light 3a is reflected by the cylindrical mirror 1 and turned into parallel light 3b. Thus, no aberrations occur in the condensed light, and the intensity of the detected light can be increased.

In the present embodiment, the polarization filter 7 and the slit 8 can be configured, for example, by providing optical elements having the following characteristics:

R27a (mm): curvature radius of the cross-sectional shape of the polarization filter 7 on the light incident surface side in the yz-plane;

R27b (mm): curvature radius of the cross-sectional shape of the polarization filter 7 on the light output surface side in the yz-plane;

Nd5 (–): refractive index of the polarization filter 7 on the center axis;

vd5 (–): Abbe number of the polarization filter 7 on the center axis;

D29 (mm): thickness of the polarization filter 7;

D30 (mm): distance between the polarization filter 7 and the cylindrical mirror 10 in the direction of the optical axis 1b of the detection optical system; and R27a=∞, R27b=∞, Nd5=1.51680, vd5=64.2, D29=2 mm, D30=85 mm.

With this configuration, the scanning range of the radiation optical system on the silicon wafer 4 is ±0 mm in the Y-direction and ±5 mm in the X-direction, which is a generous value, taking the X-Y direction on the stage 4a as a reference.

According to the present embodiment, similar effects as with Embodiment 2 are attained, and moreover by suitably disposing a polarization filter 7 in the detection optical system, it is possible to focus only the scattered light from the foreign matter selectively and efficiently, thus increasing the detection sensitivity of the surface foreign matter inspection device in comparison with Embodiment 2.

Embodiment 7

Figure 7:
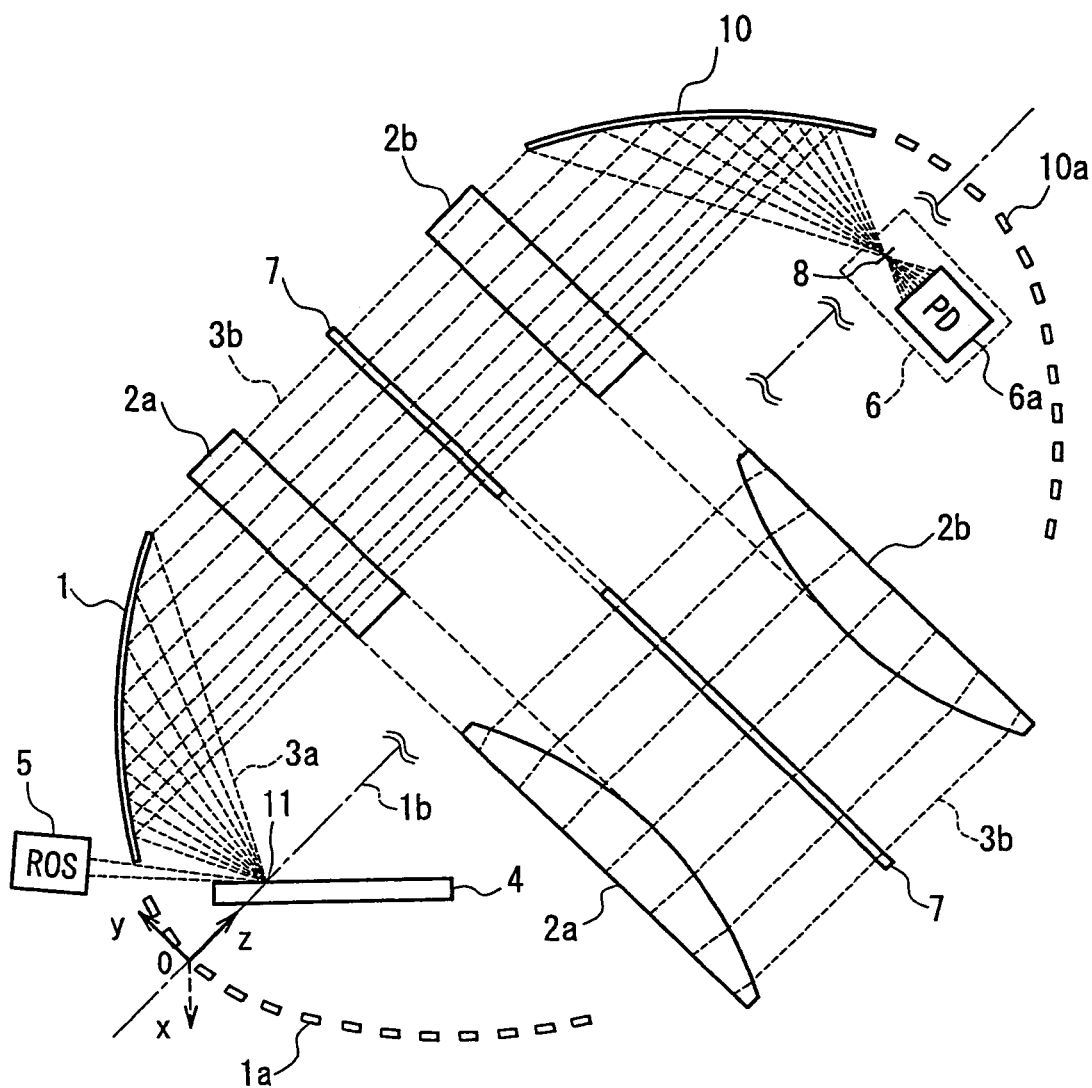
FIG. 7 is a schematic diagram showing a configuration of a surface foreign matter inspection device according to Embodiment 7 of the present invention.

FIG. 7 is a schematic diagram showing a configuration of a surface foreign matter inspection device according to Embodiment 7 of the present invention. The configuration of this device is similar to that of the device in Embodiment 5 (FIG. 5), except that the polarization filter 7 is disposed between a pair of cylindrical lenses 2a and 2b instead of between the slit 8 and the photo-detector 6a in the optical detection means 6.

In FIG. 7, the polarization filter 7 is movable and can be switched between a state in which it is placed on the light path of the condensed light and a state in which it is removed from the light path in the optical detection means 6. Other portions corresponding to FIG. 5 have been given the same numerals, and their further explanation has been omitted. Also the coordinate system is the same as in FIG. 5.

Using this device, foreign matter on the silicon wafer 4 can be inspected as follows. As in Embodiment 1, irradiation light is irradiated onto the foreign matter to generate scattered light 3a, the scattered light 3a is captured by the detection optical system 12, reflected by the cylindrical mirror 1 and turned into parallel light 3b. Then, the parallel light 3b passes through the cylindrical lens 2a and further through the polarization filter 7, and then through the cylindrical lens 2b and the intensity of the condensed light is converted into an electrical signal by the photo-detector 6a. After that, the same processing as in Embodiment 1 is performed.

In this embodiment, the same effect as in Embodiment 5 can be attained with the polarization filter 7, and foreign matter on the silicon wafer 4 and structural unevenness such as wiring or the like, can be discriminated by the polarization filter 7. It should be noted that it is preferable that the polarization filter 7 is disposed between the cylindrical mirror 1 and the cylindrical mirror 10, whose optical axes are substantially matched. Thus, no aberrations occur in the condensed light, and the intensity of the detected light can be increased.

It should be noted that if the polarization filter 7 is placed in the detection optical system 12, then it is preferable that it is placed between the cylindrical mirror 1 and the cylindrical mirror 10 in a region where the scattered light 3a has been reflected by the cylindrical mirror 1 and turned into parallel light 3b. Thus, no aberrations occur in the condensed light, and the intensity of the detected light can be increased.

In this embodiment, the cylindrical mirror 1, the cylindrical mirror 10 and the cylindrical lenses 2a and 2b can be configured by disposing optical elements having the same characteristics as those in Embodiment 5 in the same manner inside the device, and the polarization filter 7 can be configured, for example, by disposing a polarization filter having the same characteristics as the polarization filter 7 of Embodiment 6 in the same manner as in Embodiment 6.

With this configuration, the scanning range of the radiation optical system on the silicon wafer 4 is ±0 mm in the Y-direction and ±5 mm in the X-direction, which is a generous value, taking the X-Y direction on the stage 4a as a reference.

According to the present embodiment, similar effects as with Embodiment 5 are attained, and moreover by disposing a polarization filter at a suitable position inside the detection optical system 12, it is possible to focus only the scattered light from the foreign matter selectively and efficiently, thus increasing the detection sensitivity of the surface foreign matter inspection device in comparison with Embodiment 5.

Figure 8:
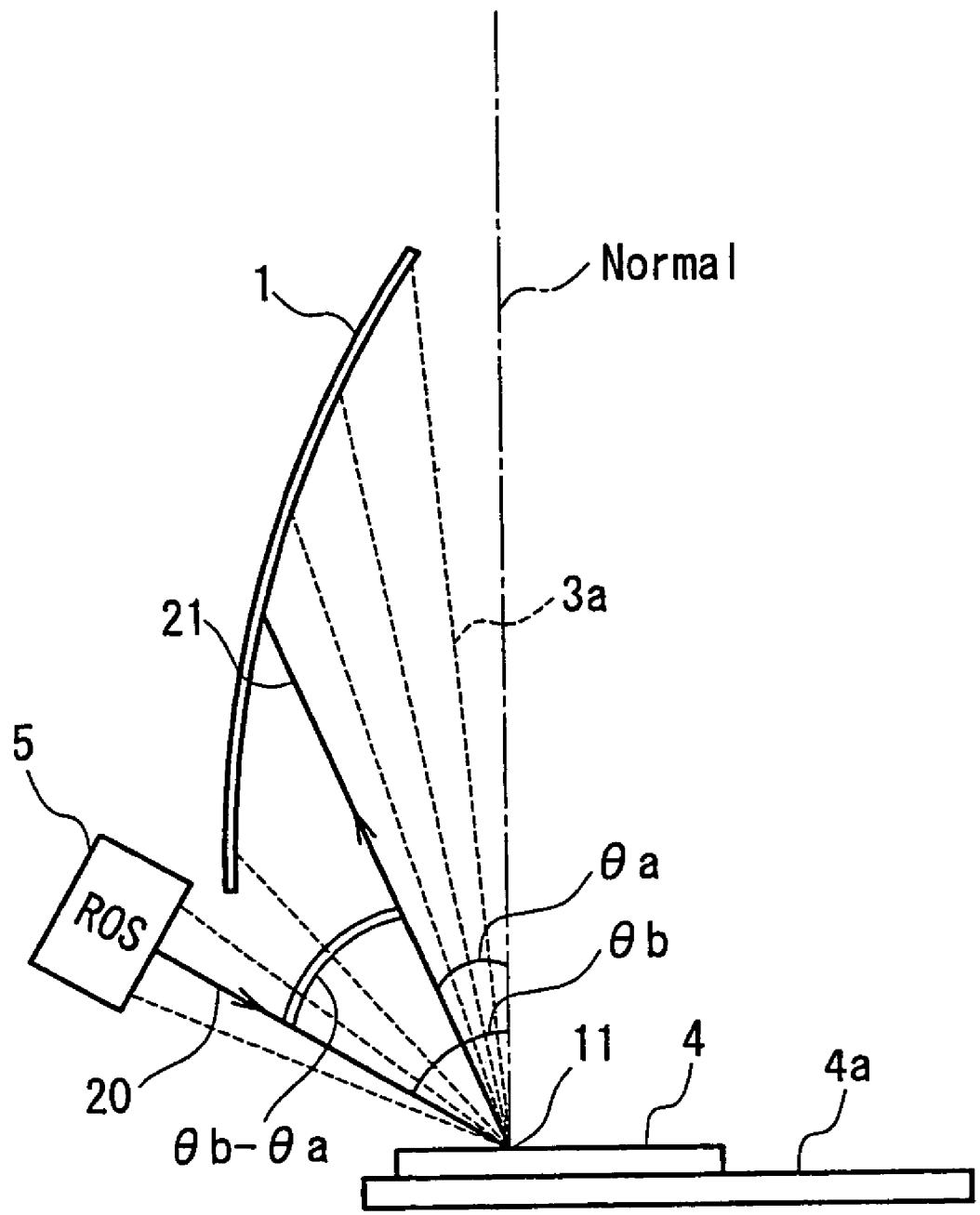
FIG. 8 is a diagram illustrating the relationship between the incidence angle θ b of irradiated light and the reflection angle θ a of scattered light.

It should be noted that in the above-described embodiments, when $\theta b$ (°) is the angle of incidence of the main light ray 20 of the light beam that is irradiated from the radiation optical system 5 onto the surface of the silicon wafer 4, and $\theta a$ (°) is the reflection angle of the main light ray 21 of the light beam (of the scattered light 3a that is scattered by the foreign matter on the silicon wafer 4) that is reflected by the cylindrical mirror 1, as shown in FIG. 8, then it is preferable that the cylindrical mirror 1 and the radiation optical system 5 are disposed such that the relationship $\theta b - \theta a < 45°$ is satisfied. This is because when $\theta b - \theta a \geq 45°$, then the cylindrical mirror 1 requires a large size, and the focusing efficiency of the scattered light 3a is decreased.

Figure 10:
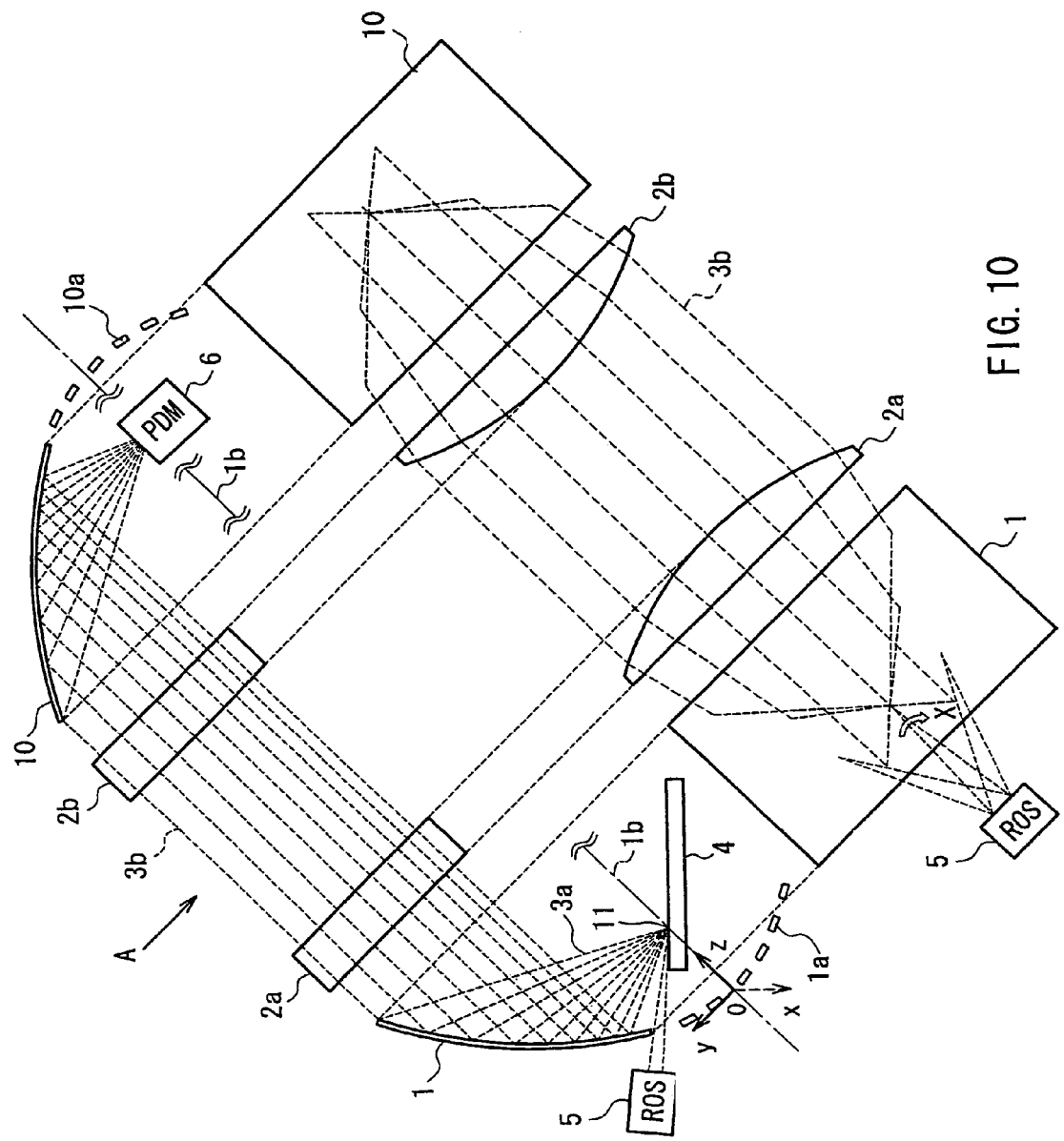
FIG. 10 is a schematic diagram showing a configuration of a surface foreign matter inspection device according to another embodiment of the present invention.

Moreover, if a laser light source is used for the radiation optical system (ROS) 5, then a configuration is possible in which the laser light is scanned in x-direction, as shown in FIG. 10, alternatively, it is also possible to use a laser light source that is oblong in the x-direction.

As described above, according to the present invention, by using a cylindrical mirror or mirrors for the detection optical system in a surface foreign matter inspection device, it is possible to increase the NA of the optical system with a simple configuration. Thus, the object point range on the object under inspection over which the detection optical system can capture reflected light can be broadened, the scanning range of the radiation optical system on the object to be inspected can be enlarged, and the distance over which irradiated light is scanned is shortened, so that the time needed for the foreign matter inspection is shortened. Moreover, a large amount of the light scattered by the foreign matter can be captured, and the detection sensitivity of the surface foreign matter inspection device can be increased.

The invention claimed is:

1. A surface foreign matter inspection device using an optical means to inspect foreign matter on an object under inspection, comprising:
   a stage on which the object under inspection is placed and moved;
   a light irradiation means for irradiating light onto a surface of the object under inspection;
   a focusing means comprising a first cylindrical mirror that reflects light scattered by foreign matter on the object under inspection and turns the reflected light into parallel light, and a condensing means for condensing the parallel light;
   an optical detection means for receiving the condensed light from the condensing means and converting an intensity of the condensed light into an electrical signal; and
   an information processing device for processing the electrical signal that is output from the optical detection means and position information regarding the foreign matter on the object under inspection.

2. The surface foreign matter inspection device according to claim 1, wherein the condensing means is a condensing lens.

3. The surface foreign matter inspection device according to claim 1, wherein the condensing means is a second cylindrical mirror whose optical axis substantially coincides with the optical axis of the first cylindrical mirror.

4. The surface foreign matter inspection device according to claim 1, wherein the direction in which light is irradiated by the light irradiation means and the direction of the lens effect of the first cylindrical mirror are substantially perpendicular.

5. The surface foreign matter inspection device according to claim 3, wherein the cross-sectional shapes of the first and second cylindrical mirrors in the direction of their lens effect are substantially parabolic.

6. The surface foreign matter inspection device according to claim 3, wherein an angle $\theta$ (°) defined by the optical axes of the first and second cylindrical mirrors and the surface of the object under inspection is $0° < \theta < 60°$.

7. The surface foreign matter inspection device according to claim 1, wherein the optical detection means comprises:
   a slit through which light from the focusing means passes;
   a photo-detector that receives the light from the slit and converts its optical intensity into an electrical signal; and
   a polarization filter that is disposed between the slit and the photo-detector.

8. The surface foreign matter inspection device according to claim 1, wherein the focusing means comprises a polarization filter disposed between the first cylindrical mirror and the condensing means.

9. The surface foreign matter inspection device according to claim 1, wherein the focusing means further comprises a cylindrical lens having a columnar surface, wherein parallel light that is reflected by the first cylindrical mirror passes through the cylindrical lens, and is then condensed by the condensing means.

10. The surface foreign matter inspection device according to claim 9, wherein the cylindrical lens is configured as a pair of cylindrical lenses whose columnar surfaces are opposed to each other, and whose directions of the lens effect substantially coincide with each other.

11. The surface foreign matter inspection device according to claim 9, wherein the direction of the lens effect of the cylindrical lens is substantially perpendicular to the direction of the lens effect of the cylindrical mirror.

12. The surface foreign matter inspection device according to claim 9, wherein the cross-sectional shape of the cylindrical lens in the direction of its lens effect is non-circular arc-shaped.

13. The surface foreign matter inspection device according to claim 9, wherein, when $\theta b$ (°) is the angle of incidence of a main light ray of the light beam that is irradiated onto the surface of the object under inspection, and $\theta a$ (°) is the reflection angle of the main light ray of the light beam scattered by the foreign matter on the object under inspection that is reflected by the cylindrical mirror in the focusing means, then the relationship $\theta b - \theta a < 45°$ is satisfied.

* * * * *